United States Patent [19]

Gesslein et al.

[11] Patent Number: 4,978,526

[45] Date of Patent: Dec. 18, 1990

[54] HAIR AND SKIN CONDITIONING AGENTS AND METHODS

[75] Inventors: Bruce W. Gesslein, Piscataway, N.J.; Jacob J. Guth, Upper Black Eddy, Pa.; Gilbert R. Mintz, Cranbury; Gale M. Reinhart, Belford, both of N.J.; Laurence R. Smith, New York, N.Y.

[73] Assignee: Inolex Chemical Company, Philadelphia, Pa.

[21] Appl. No.: 249,632

[22] Filed: Sep. 26, 1988

[51] Int. Cl.$^5$ .................... A61K 7/075; A61K 7/15; A61K 7/48

[52] U.S. Cl. ........................... 424/70; 424/73; 252/DIG. 13; 514/755; 514/846; 514/847; 514/848; 514/873

[58] Field of Search .................... 424/73, 70; 514/788, 514/846, 847, 848, 873; 252/DIG. 13

[56] References Cited

U.S. PATENT DOCUMENTS

| | | | |
|---|---|---|---|
| 2,589,674 | 3/1952 | Cook et al. | 260/404.5 |
| 3,577,528 | 5/1971 | Yonkers et al. | 424/70 |
| 3,697,452 | 10/1972 | Olson et al. | 252/545 |
| 3,755,559 | 8/1973 | Hewitt et al. | 424/70 |
| 3,849,348 | 11/1974 | Hewitt et al. | 252/547 |
| 3,959,461 | 5/1976 | Bailey et al. | 424/70 |
| 4,012,398 | 3/1977 | Conner et al. | 260/404.5 |
| 4,183,917 | 1/1980 | Iwao et al. | 424/70 |
| 4,252,695 | 2/1981 | Homma et al. | 252/547 |
| 4,592,907 | 6/1986 | Akimoto et al. | 424/70 |
| 4,673,568 | 6/1987 | Grollier et al. | 424/47 |
| 4,726,945 | 2/1988 | Patel et al. | 424/70 |

OTHER PUBLICATIONS

Kirk-Othmer Encyclopedia of Chemical Technology, 3rd Ed, vol. 19, pp. 521-531, 1982.

*Primary Examiner*—Merrell C. Cashion, Jr.
*Assistant Examiner*—Susan S. Rucker
*Attorney, Agent, or Firm*—Panitch Schwarze Jacobs & Nadel

[57] ABSTRACT

Alkyl or alkylamido dimethyl 2,3-dihydroxypropyl ammonium salts may be used in hair and skin conditioning compositions and methods to provide improved manageability, static control, and ease of wet and dry combing when applied to hair, particularly human scalp hair, and smooth and lubricated surfaces with pleasant after-feel when applied in topical conditioner compositions to the human skin. The hair conditioning formulations may include styling, cleaning and rinsing compositions such as gels, mousses, sprays, lotions, glazes and shampoos, while the skin conditioning compositions may include moisturizing creams and lotions, bath oils, liquid cleaners, body mousses or bath gels, as well as alcoholic or hydroalcoholic astringents, toners, pre-electric shave conditioners, after-bath splashes and fragrance products. A preferred quaternary according to the invention is oleamidoproyl dimethyl 2,3-dihydroxypropyl ammonium chloride, which forms exceptionally stable, clear, dilutable gels.

28 Claims, No Drawings

HAIR AND SKIN CONDITIONING AGENTS AND METHODS

FIELD OF THE INVENTION

The present invention relates to hair and skin conditioning formulations with certain improved properties. More particularly, the invention is directed to the use in hair and skin conditioning formulations of known wetting or emulsifying agents which impart improved lubricity and emolliency to the skin and hair.

BACKGROUND OF THE INVENTION

Quaternary ammonium salts have been known for over 20 years to be effective as skin and hair conditioning agents. In applications of this type a quaternary, containing a long chain alkyl group of from 8 to 24 carbons, binds to the surface of the skin or hair and by virtue of the hydrophobic nature of the alkyl chain serves to "lubricate" the substrate surface. This lubrication manifests itself as a smooth, silky after-feel when the quaternaries are applied to skin or in the reduction of force needed to achieve combing when the compounds are applied to hair.

Some of the more recent examples of the use of quaternaries in the skin and hair conditioning area can be seen in U.S. Pat. No. 4,183,917 to Iwao et al. who disclose a hair conditioner composition containing the quaternary distearyl dimethyl ammonium chloride and U.S. Pat. No. 3,577,528 to McDonough et al. which describes the use of unsaturated long chain quaternaries in a two phase hair conditioner.

Patel et al. describe in U.S. Pat. No. 4,726,945 a conditioning system containing a mixture of a diquaternary ammonium salt, stearyl alcohol, stearamidopropyl dimethylamine, and cyclomethicone which is reported to not build up on the hair and to be able to be removed during washing. Furthermore, Connor et al. in U.S. Pat. No. 4,012,398 teach that the product achieved by reacting ethylene chlorohydrin or bromohydrin with an amide obtained through the condensation of mink oil with either dimethylaminopropylamine or diethylaminopropylamine exhibits conditioning properties as well as emolliency.

The patent literature is replete with references to the conditioning properties of quaternaries, but generally speaking, those materials which demonstrate acceptable conditioning exhibit the negatives of build-up, defoaming of surfactant systems, incompatibility with water-based materials, incompatibility with anionic surfactants, and such low levels of water solubility as to make a clear shampoo or similar formulation an impossibility.

The class of compounds known as alkylamido dimethyl 2,3-dihydroxypropyl ammonium salts has been described in U.S. Pat. No. 2,589,674 to Cook et al. as being useful as wetting agents, detergents, emulsifying agents, germicides and fungicides, but their use has not been described in hair or skin conditioners.

BRIEF SUMMARY OF THE INVENTION

According to the present invention, it has been found that the alkyl or alkylamido dimethyl 2,3-dihydroxypropyl ammonium salts provide improved manageability, static control, and ease of wet and dry combing when added to conditioning compositions for topical application to hair, particularly human scalp hair. Also according to the invention, it has been found that the alkyl or alkylamido dimethyl 2,3-dihydroxypropyl ammonium salts provide a smooth and lubricated surface with pleasant after-feel to the skin when used in topical conditioner compositions applied to the human skin.

More particularly, the compositions and methods according to the present invention contain effective amounts of quaternary ammonium salts of the formula:

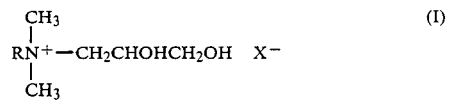

wherein R is an alkyl group of about 7 to about 24 carbon atoms or an alkylamido group of the formula:

wherein R, is an alkyl group of about 7 to 24 carbon atoms, Y is hydrogen or lower alkyl, z is about 2 to about 6, and $X^-$ is a counter ion selected from a carboxylate group (i.e. $CO_2^=$) and anions of strong acids.

In the case of hair conditioning formulations, the quaternary ammonium salts of formula I may be used in styling, cleaning and rinsing compositions such as gels, mousses, sprays, lotions, glazes, and shampoos. In the case of skin conditioning formulations, the quaternary ammonium salts of formula I may be used in compositions such as moisturizing creams and lotions, bath oils, liquid cleaners, body mousses, or bath gels, as well as astringents, toners, pre-electric shave conditioners, after-bath splashes and fragrance products. The salts of formula I are particularly useful in the formulation of personal care products in the form of clear, stable solutions which do not leave build-up on the hair or skin.

DETAILED DESCRIPTION OF THE PREFERRED EMBODIMENTS

As noted above, the alkylamido dimethyl 2,3-dihydroxypropyl ammonium salts of formulas I and II above are among the compounds described and claimed in U.S. Pat. No. 2,589,674 to Cook et al. These quaternary ammonium salts may be made by the methods of that patent or by other methods which will be evident to those skilled in the art. The corresponding alkyl dimethyl 2,3-dihydroxypropyl ammonium salts of formula I wherein R is an alkyl group, may be prepared by analogous methods which will be evident to those skilled in the art.

For ease of reference herein, the alkyl dimethyl 2,3-dihydroxypropyl ammonium salts will sometimes be referred to as the G-series of quaternaries and the corresponding alkylamido dimethyl 2,3-dihydroxypropyl ammonium salts will sometimes be referred to as the AMG-series of quaternaries. The number or letter following G or AMG will signify the number of carbon atoms in the R or R, alkyl group. For example, G-10 refers to an alkyl dimethyl 2,3-dihydroxypropyl ammonium salt in which R is decyl, namely 10 carbon atoms. Similarly, AMG-M refers to an alkylamido dimethyl 2,3-dihydroxypropyl ammonium salt derived from myristic acid. Unless indicated otherwise, the particular salt referred to is the chloride salt ($X^{31} = Cl^{31}$), but it will be understood that other anions besides chloride could be used, as discussed more fully below.

In the G-series, R may be a straight or branched-chain alkyl group of 7 to 24 carbon atoms, and preferably 12 to 18 carbon atoms. The alkyl group may also be substituted or partially unsaturated, but it is preferred that the alkyl group be straight chain, unsubstituted and fully saturated.

Similarly, the R' group of the alkylamido moiety of formula II may be straight or branched-chain, substituted and/or partially unsaturated, but it is preferred that straight chain, unsubstituted and fully saturated alkyl groups of 7 to 24 carbon atoms, and preferably 12 to 18 carbon atoms be used. The Y group of the alkylamido moiety may be hydrogen or lower (i.e., $C_1$ to $C_6$) alkyl, but is preferably hydrogen, methyl or ethyl, and most preferably, a hydrogen atom. The alkylene chain which attaches the alkylamido group to the quaternary nitrogen atom is preferably a $C_1$ to $C_6$ straight carbon chain, and most preferably, a propyl ($C_3$) chain.

In the quaternary ammonium salt of formula I, the counter ion (anion) of the quaternary salt is represented by $X^-$. This counter ion may be either a carboxylate ($CO_2^=$) group or an anion of a strong acid. Suitable counter ions derived from strong acids include chloride, bromide, sulfate, phosphate, etc., with the chlorides being preferred.

The preferred alkyl or alkylamido dimethyl 2,3-dihydroxypropyl ammonium salts for use in the present invention will vary depending upon the particular hair or skin conditioning formulation in which the quaternary salt is used. However, in general, the alkylamido salts derived from oleic, myristic or lauric/cocyl (also referred to as whole coconut) acids are preferred, namely, oleamidopropyl dimethyl 2,3-dihydroxypropyl ammonium chloride (AMG-O), myristylamidopropyl dimethyl 2,3-dihydroxypropyl ammonium chloride (AMG-M), or cocoamidopropyl dimethyl 2,3-dihydroxypropyl ammonium chloride (AMG-WC).

The above-described quaternary ammonium salts may be combined with a wide variety of other cosmetic ingredients to produce a broad range of functional formulations useful in skin and hair applications. For example, as will be described and illustrated more fully below, the above quaternary salts may be mixed with alkyl sulfates, betaines, or fatty amides to form conditioning shampoos and bath gels; with aminoxides, cellulosics, or polyols to form clear hair conditioners; ethanol, water, or polyols to form astringents, toners, and after-bath splashes; paraffinic oils, GMS, fatty alcohols, or water to form skin moisturizers; fatty quaternaries or cationic protein derivatives to form clear, dilutable bath or hair gels. Other types of hair and/or skin conditioning formulations which may benefit from the use of the quaternary salts of the present invention for application to human skin and/or mammalian hair, particularly human scalp hair, will be evident to those skilled in the art in view of the present disclosure.

Thus, it has been found that alkyl or alkylamido dimethyl 2,3-dihydroxypropyl ammonium salts of the type shown above provide excellent skin and hair conditioning benefits. These salts can be used to provide clear, stable, high foaming conditioning shampoos and rinses without the build-up so commonly seen with typical conditioning materials. The excellent compatibility of these cationic salts with all ionic classes of compounds and the solubilizing properties of these salts allows for their combination with fatty quaternaries of low solubility and/or anionic surfactants to form clear, high performance conditioning liquids and gels.

When used in hair conditioning formulations, such as shampoos, rinses or styling products, the formulations according to the present invention impart manageability, static control, and ease of wet and dry combing which are comparable or superior to conventional formulations, but without the usual build-up or residues left in the hair, and without affecting the foaming of the shampoo or other instability problems which are typical of conventional formulations. It is also possible to use these quaternary salts in connection with other fatty quaternaries, cationic collagen derivatives, metallic, inorganic or organic salts to produce conditioning formulations in the form of clear, stable liquids and gels, and in some cases, dilutable gels.

In the case of skin conditioning formulations of the present invention, the use of the above quaternary salts imparts a smooth, soft, silky feel to the skin, whether applied to the skin in the form of an aqueous cream, lotion, bath oil, liquid cleaner, body mousse or other formulation. Also, similar effects are achieved using the above quaternary salts in skin conditioners based on alcoholic or hydroalcoholic vehicles, such as astringents, toners, pre-electric shave conditioners, after-bath splashes, fragrance products such as perfumes and colognes, etc. As with the hair conditioning formulations, the superior solubility and stability properties of the above quaternary salts makes possible the preparation of skin conditioners in the form of clear, stable liquids and gels.

Still further, the above quaternary salts may be used in hair and skin formulations as primary cationic emulsifiers of the medium to high hydrophilic/lipophilic balance (HLB) range in a wide variety of emulsion systems. Alternatively, in view of the compatibility of the salts with other ionic classes of compounds, these quaternary salts may be used in combination with other cationic emulsifiers or to replace all or a portion of the conventional cationic emulsifier of a given formulation.

The amount of the above quaternary salt to be included in a particular formulation will depend on a number of factors, including the nature of the formulation, the intended function of the salt in the formulation, the amounts of other ionic agents in the formulation, etc. In general, the above quaternary salts to be effective for the intended functions and benefits should be present in amounts of about 0.5 to 10 weight percent, and preferably about 1 to 7 weight percent of the total composition.

The invention will now be described in more detail with reference to the following specific, non-limiting examples:

Comparative Results

In order to demonstrate the effectiveness of the alkyl and alkylamido dimethyl 2,3-dihydroxypropyl ammonium salts for use in the hair and skin conditioning compositions and methods of the present invention, the following comparative tests were performed with various of these quaternary salts, and the results are set forth in the accompanying tables, as indicated below. The particular quaternary salts are designated in the tables by the G-series and AMG-series designations as described above.

EXAMPLE I

Conditioning effects were determined by application of a 2% aqueous solution of the quaternary ammonium salt to the appropriate hair tress. The intact hair was commercially available virgin, previously untreated European hair tresses, while the damaged hair was ammoniated, peroxide-treated hair tresses. Each tress was then stroked 30 times to effect distribution of the conditioning agent. The solution was allowed to remain on the tress for two minutes, whereupon the tress was rinsed with clear water for 15 seconds, towel blotted and combed by five panelists for evaluation. A rating on a scale of 1 to 5 was then given by the panelists for each test parameter, a rating of 1 being the least desirable effect and 5 being the most desirable. Humidity was not controlled during this experiment. The results are given in Table I.

Table I compares the detangling effort and wet and dry combing effort for hair tresses treated with selected G or AMG-series materials. The results demonstrate that with respect to these three parameters many of the quaternaries perform as well or better than the water control when tested on intact and/or damaged hair tresses. It is apparent that oleamidopropyl dimethyl 2,3-dihydroxypropyl ammonium chloride has better hair conditioning properties than the other compounds tested.

EXAMPLE II

The tests of Example I were repeated with another panel using the best quaternary salt of Example I, namely oleamidopropyl dimethyl 2,3-dihydroxypropyl ammonium chloride in comparison to three quaternary ammonium salts commonly used in prior hair conditioning formulations. Using the same rating system, the results are shown in Table II, which indicates that AMG-0 compares favorably in these test results to conventional quaternary ammonium salts. It should be noted that AMG-0 performed as well as the stearaminodopropyl propylene glycol diammonium cationic and almost as well as stearalkonium chloride, a commonly used conditioning agent in hair shampoos, in all aspects of conditioning.

EXAMPLE III

The build-up or residues of quaternary ammonium salts on the hair was demonstrated using three quaternary ammonium salts of the invention compared to two prior art quaternary salts using the well-known Rubine-Dye test method developed by Sandoz. All materials tested were used at a concentration of 1 weight percent of the salt in water. The salts were ranked on a scale of 1 to 5, with 1 representing the most desirable (little or no build-up or residue) and 5 indicating the least desirable (most build-up). As shown in Table III, the quaternaries of the invention show minimal, if any, build-up on the hair after repeat applications.

EXAMPLES IV

The effect of the quaternary salts of the invention on the foaming properties of a typical shampoo foamer, namely CAP betaine (commercially available under the trademark LEXAINE C from Inolex Chemical Company, were demonstrated using 0.2 weight percent solutions of the surfactant system in water, with the surfactant system consisting of a 5:2 weight ratio of LEXAINE C to the quaternary of choice. Foam height measurements were obtained by agitation of 50 mls of the 0.2 percent solution for 60 seconds. Drain volume was the amount of liquid draining out of the generated foam after 30 seconds. The results are set forth in Table IV.

Typically, quaternary ammonium salts that have been found to be effective conditioning agents when incorporated into shampoos or rinses, have the disadvantage that the structures severely depress the foaming properties of the primary surfactants in the formulation and may cause instability of the product itself, exhibiting a disappointing volume of foam on application to the scalp. The alkyl/alkylamido dimethyl 2,3-dihydroxypropyl ammonium salts, being much more water soluble and compatible with all ionic classes of surfactants commonly used in shampoos, do not significantly depress the foaming properties of the primary surfactant, nor cause instability. The end result of this effect is a much more attractive and cosmetically elegant formulation.

In Table IV alkylamido dimethyl 2,3-dihydroxypropyl ammonium salts and two of the quaternary ammonium salts more commonly used as conditioning agents are compared as to their effects on the foaming properties of a principal surfactant, in this case a cocoamidopropyl betaine (CAP betaine). These results indicate that when one of the AMG-series of materials is formulated with another surfactant, it does not severely depress the foam properties of the betaine as determined by foam height measurements. In contrast, the presence of stearalkonium chloride in a formulation has a marked effect (decreases 4-fold) on the foaming properties relative to the CAP betaine control. These results clearly show the superiority of the alkylamido dimethyl 2,3-dihydroxypropyl ammonium salts in supporting the foaming characteristics of primary surfactants, not only in terms of the amount of foam generated (as measured by foam height) but also in terms of the quality or the density of the foam (as measured by the volume of liquid remaining in the foam).

EXAMPLE V

Foaming tests were conducted as in Example IV except that each of the quaternary salts and prior art surfactants listed in Table V was used alone as a surfactant at a concentration of 0.2 weight percent in water. However, duplicate tests were run on each surfactant, one set of tests being without the presence of sebum, and the other set of tests being run with each composition containing 0.1 ml of an artificial sebum consisting of 20 percent lanolin, 5 percent linoleic acid and 75 percent ethylacetate added to each 50 ml surfactant solution. The data in Table V indicate that the alkyl/alkylamido dimethyl 2,3-dihydroxypropyl ammonium salts exhibit fairly good foaming properties in their own right, although the ability to foam in the presence of sebum loads is somewhat limited. In general, it can also be seen that the AMG-series of quaternaries produces high foam volumes which are more stable both with and without sebum.

EXAMPLE VI

A series of surfactant/quaternary mixtures was prepared at a total actives concentration of 10 weight percent, and a surfactant/quaternary ratio of 10:1. As indicated in Table VI, the surfactants used in combination with the quaternaries of the present invention were sodium lauryl sulfate (SLS), ammonium lauryl sulfate (ALS), sodium lauryl ether sulfate (SLES), ammonium lauryl ether sulfate (ALES), CAP betaine, CAP sulfobetaine, and triethanolamine lauryl sulfate (TEALS). As indicated, all of the combinations produced clear solutions, and when submitted to the Draize Primary Occular and Skin Irritation procedures were demonstrated to be very mild and non-irritating.

The exceptional compatibility of the alkyl/alkylamido dimethyl 2,3-dihydroxypropyl ammonium salts with various ionic classes of surfactants (particularly the anionic types) allows the formulator a great deal of latitude in the choice of the principal surfactants used to prepare clear, high foaming, stable conditioning formulations. It is evident from Table VI that, in combination with a wide variety of surfactants, all of the G and AMG-series of quaternaries form clear and stable mixtures.

EXAMPLE VII

The AMG-O quaternary forms a stable gel when sodium chloride is present at 15%. These gels remain stable and clear at 20% sodium chloride, the highest salt concentration tried. In contrast, AMG-M and AMG-WC do not form gels upon addition of sodium chloride up to a final concentration of 20%. In addition, the oleayl analog produces a clear gel in a mixture with metallic and organic salts.

EXAMPLE VIII

To test the pH stability of the quaternaries, 1% actives aqueous solutions were prepared. Both the G-series and AMG-series were completely compatible with changes in pH down to 2 adjusted with citric acid or increases in pH to 12 with the addition of TEA (triethanolamine).

TABLE I

Comparison of the Conditioning Properties of Selected G-Series and AMG-Series of Quaternaries

| Conditioning Parameter | G-10 | G-14 | AMG-10 | AMG-M | AMG-O | Water |
|---|---|---|---|---|---|---|
| Detangling | | | | | | |
| Intact Hair | 1.0 | 2.0 | 3.0 | 1.0 | 4.0 | 2.0 |
| Damaged Hair | 1.0 | 2.0 | 2.0 | 2.0 | 4.0 | 1.0 |
| Wet Combing | | | | | | |
| Intact Hair | 2.8 | 3.0 | 2.8 | 3.0 | 3.5 | 2.0 |
| Damaged Hair | 1.6 | 3.5 | 1.6 | 3.3 | 3.6 | 1.0 |
| Dry Combing | | | | | | |
| Intact Hair | 2.8 | 2.8 | 3.1 | 3.0 | 3.3 | 2.9 |
| Damaged Hair | 2.7 | 2.7 | 2.5 | 3.2 | 3.6 | 1.7 |
| Static Control | | | | | | |
| Intact Hair | 1.6 | 1.8 | 2.4 | 1.8 | 2.9 | 2.4 |
| Damaged Hair | 2.0 | 2.0 | 2.6 | 2.4 | 3.9 | 2.2 |

TABLE II

A Comparison of Conditioning Properties of Selected Quaternaries

| Conditioning Parameter | Stearalkonium Chloride | AMG-O | Stearamidopropyl PG Diammonium Chloride Phosphate | Quaternium 22 | Water |
|---|---|---|---|---|---|
| Detangling | | | | | |
| Intact Hair | 4.0 | 3.0 | 3.5 | 1.0 | 2.0 |
| Damaged Hair | 4.0 | 3.0 | 3.5 | 1.0 | 1.0 |
| Wet Combing | | | | | |
| Intact Hair | 4.0 | 3.7 | 3.2 | 2.6 | 1.7 |
| Damaged Hair | 4.0 | 3.6 | 3.6 | 1.4 | 1.1 |
| Dry Combing | | | | | |
| Intact Hair | 3.9 | 3.3 | 3.7 | 3.0 | 1.9 |
| Damaged Hair | 4.0 | 3.3 | 3.6 | 2.9 | 2.0 |
| Static Control | | | | | |
| Intact Hair | 3.9 | 3.3 | 3.3 | 1.6 | 1.5 |
| Damaged Hair | 4.0 | 3.1 | 2.3 | 3.1 | 1.6 |

TABLE III

The Lack of Build-Up On The Hair As Demonstrated by the Rubine Dye Test

| | No. of Treatments: | Build Up | |
|---|---|---|---|
| | 1 | 5 | 10 |
| Stearalkonium Chloride | 4 | 5 | 5 |
| Quaternium 22 | 3 | 4 | 4 |
| Oleamidopropyl Dimethyl 2,3-Dihydroxy propyl Ammonium Chloride | 1 | 1 | 2 |
| Cocoamidopropyl Dimethyl 2,3-Dihydroxy propyl Ammonium Chloride | 1 | 1 | 1 |
| Myristylamidopropyl Dimethyl 2,3-Dihydroxy propyl Ammonium Chloride | 1 | 1 | 1+ |

Number of treatments = treating and rinsing prior to rubine dye.

TABLE IV

Foaming Properties of Surfactant Systems Containing Selected Quaternaries

| Surfactant/Conditioner | Foam Height (ml at T = O) | Drain Vol (ml at T = 30 sec) |
|---|---|---|
| CAP betaine/none | 190 | 8.5 |
| CAP betaine/AMG-M | 178 | 20.8 |
| CAP betaine/AMG-WC | 178 | 22.0 |
| CAP betaine/AMG-O | 186 | 12.8 |
| CAP betaine/Stearalkonium Chloride | 50 | 41.3 |
| CAP betaine/Stearamidopropyl PG- | 111 | 32.0 |

TABLE IV-continued
Foaming Properties of Surfactant Systems Containing Selected Quaternaries

| Surfactant/Conditioner | Foam Height (ml at T = O) | Drain Vol (ml at T = 30 sec) |
|---|---|---|
| Dimonium Chloride Phosphate | | |

TABLE V
Foaming Properties of the Alkyl/Alkylamidodimethyl 2,3-dihydroxypropyl Ammonium Salts

| | Foam Height | | Drain Volume | |
|---|---|---|---|---|
| Surfactant | Without Sebum | With Sebum | Without Sebum | With Sebum |
| AMG-M | 192 | 127.0 | 10.3 | 34.3 |
| AMG-WC | 193 | 63.0 | 15.3 | 32.7 |
| AMG-O | 177 | 33.3 | 17.0 | 41.0 |
| G-14 | 188 | 28.3 | 9.7 | 42.3 |
| G-WC | 190 | 41.7 | 9.7 | 36.7 |
| G-18 | 187 | 27.5 | 15.0 | 44.5 |
| CAP-betaine | 193 | 122.0 | 5.8 | 28.3 |
| Sodium Lauryl Sulfate | 192 | 121.7 | 10.0 | 31.7 |

TABLE VI
Stability of Surfactant/Quaternary Mixtures

| Surfactant | G-10 | G-12 | G-WC | G-18 | AMG-M | AMG-WC | AMG-O |
|---|---|---|---|---|---|---|---|
| SLS | Clear | Clear | Clear | Clear | Clear | Clear | Clear |
| ALS | Clear | Clear | Clear | Clear | Clear | Clear | Clear |
| SLES | Clear | Clear | Clear | Clear | Clear | Clear | Clear |
| ALES | Clear | Clear | Clear | Clear | Clear | Clear | Clear |
| CAP betaine | Clear | Clear | Clear | Clear | Clear | Clear | Clear |
| CAP sulfobetaine | — | — | — | — | Clear | Clear | Clear |
| TEALS | — | — | — | — | Clear | Clear | Clear |

Hair Care Formulas

The following are a few examples of finished formulations which demonstrate the utility of the alkyl/alkylamido dimethyl 2,3-dihydroxypropyl ammonium salts in clear, stable, conditioning agents or conditioning shampoos.

EXAMPLE A—Clear Conditioner

Almost every member of the G or AMG-series can be used in this formulation. However, the preferred quaternary is oleamidopropyl dimethyl 2,3-dihydroxypropyl ammonium chloride.

| Ingredients | % W/W |
|---|---|
| Part A | |
| Deionized Water | 86.39 |
| Hydroxyethyl cellulose | 0.70 |
| Glycerine | 5.00 |
| Propylene Glycol | 2.00 |
| Methylparaben | 0.20 |
| Part B | |
| Oleamidopropyl Dimethyl 2,3-dihydroxypropyl Ammonium Chloride | 5.71 |
| | 100.00 |

Procedure:

Disperse the hydroxyethyl cellulose in water. Add the remaining ingredients in Part A. Mix until clear and add Part B.

EXAMPLE B—Conditioning Shampoo

Almost every member of either the G-series or the AMG-series can be used in this formulation. However, AMG-O, AMG-WC and AMG-14 are preferred.

| Ingredients | % W/W |
|---|---|
| Part A | |
| Deionized Water | 58.00 |
| TEALS (triethanolamine lauryl sulfate) | 25.00 |
| Cocoamidopropyl betaine | 10.00 |
| Methylparaben | 0.15 |
| Oleamidopropyl dimethylamine | 0.30 |
| Part B | |
| Oleamidopropyl Dimethyl 2,3-dihydroxypropyl Ammonium Chloride | 5.71 |
| | 100.00 |

Procedure:

Heat and mix the ingredients in Part A except for the oleolamidopropyl dimethylamine to 65° C. Adjust the pH to 5.0 with citric acid. Add the oleolamidopropyl dimethylamine and mix until the solution clears. Add the oleamidopropyl dimethyl 2,3-dihyrodxypropyl ammonium chloride and mix until uniform.

EXAMPLE C—AMG-WC Clear Conditioner

This uncommon oil-free clear conditioner is especially for hair that needs good conditioning and extra body. AMG-WC furnishes excellent wet and dry combability and softness to the hair without the typical heavy film associated with many conditioners. Although AMG-WC is highly substantive, it will not build up through repeat applications. This product leaves even limp, fine hair manageable, clean and lively.

| Ingredients | % W/W |
|---|---|
| Part A | |
| Deionized Water | 80.65 |
| Hydroxypropylmethyl cellulose | 0.75 |
| Part B | |
| Myristamine Oxide | 10.00 |
| Cocoamidopropyl Dimethyl 2,3-dihydroxypropyl ammonium Chloride | 5.00 |
| Propylene Glycol USP | 3.00 |
| Methylparaben | 0.30 |
| Propylparaben | 0.10 |
| Fragrance | 0.20 |
| Citric Acid to pH | 4.5 +/− 0.2 |
| | 100.00 |

Procedure:

Charge vessel with water and heat to 75° C. Dust hydroxypropylmethyl cellulose into water with agitation. When completely hydrated, cool to 35° C. Add Part B to batch and adjust pH.

Skin Care Formulas

The following are a few examples of finished formulations which demonstrate the utility of the alkyl/alkylamidodimethyl2,3-dihydroxypropyl ammonium salts in skin creams, lotions, hydro alcohols, moisturizers, conditioners and skin mousses.

EXAMPLE 1—AMG-O Moisturizer

This light, elegant moisturizing cream applies with a rich lubriciousness and dries to a soft, smooth, nontacky feel. Oleamidopropyl dimethyl 2,3dihydroxypropyl ammonium chloride is the primary cationic emulsifier with the added benefit of emolliency. This product may be useful as a day moisturizer, a hand and body cream, or a baby cream.

| Ingredients | % (W/W) |
|---|---|
| Part A | |
| Deionized Water | 66.9 |
| Hydroxyethyl Cellulose | 0.3 |
| Glycerine | 3.0 |
| Propylene Glycol | 2.0 |
| Methylparaben | 0.2 |
| Oleamidopropyl Dimethyl 2,3 Dihydroxypropyl Ammonium Chloride | 6.3 |
| Part B | |
| Propylene Glycol Dipelargonate | 15.0 |
| Glyceryl Stearate | 2.0 |
| Myristyl Myristate | 1.0 |
| Stearyl Alcohol | 2.0 |
| Cetyl Alcohol | 1.0 |
| Propylparaben | 0.1 |
| Part C | |
| Fragrance | 0.2 |
| | 100.0 |

Procedure

Charge batch vessel with water (Part A). Begin mixing and heating to 78° C. +/− 2° C. Dust in cellosize. When completely hydrated, add remaining mateial of Part A to batch. Combine Part B in a separate vessel and heat to 78° C. +/− 2° C. When uniform slowly add Part B to Part A maintaining mixing and temperature. Allow to mix at 78° C. for 15 minutes. Cool to 40° C. and add Part C to batch. Cool to room temperature.

EXAMPLE 2—Cationic Lotion

| Ingredients | % (W/W) |
|---|---|
| Part A | |
| Deionized water | 78.93 |
| Hydroxyethylcellulose | 0.70 |
| Glycerine | 5.00 |
| Propylene Glycol | 2.00 |
| Methylparabens | 0.20 |
| Cocoamidopropyl Dimethyl 2,3-Dihydroxypropyl Ammonium Chloride | 2.57 |
| Part B | |
| Glyceryl Stearate | 4.00 |
| Mineral Oil | 5.00 |
| Lanolin 2 | 1.00 |
| Cetyl Alcohol | 0.50 |
| Propylparaben | 0.10 |
| | 100.00 |

Procedure:

Disperse gum in water and add remaining ingredients of Part A with mixing. Heat Part A and Part B separately to 78°–80° C. Add Part B to Part A with mixing cool to 30° C.

EXAMPLE 3—Clear Spray Conditioner

| Ingredients | % (W/W) 1 | 2 | 3 |
|---|---|---|---|
| Part A | | | |
| Deionized water | 83.14 | 83.14 | 83.14 |
| Hydroxyethyl Cellulose | 0.70 | 0.70 | 0.70 |
| Glycerine | 5.00 | 5.00 | 5.00 |
| Propylene Glycol | 5.00 | 5.00 | 5.00 |
| Methyl Parabens | 0.15 | 0.15 | 0.15 |
| Preservative | 0.30 | 0.30 | 0.30 |
| Part B | | | |
| Oleamidopropyl Dimethyl 2,3 Dihydroxypropyl Ammonium Chloride | 5.71 | 0.00 | 0.00 |
| Cocoamidopropyl Dimethyl 2,3-Dihydroxypropyl Ammonium Chloride | 0.00 | 5.71 | 0.00 |
| Myristylamidopropyl Dimethyl 2,3 Dihydroxypropyl Ammonium Chloride | 0.00 | 0.00 | 5.71 |
| | 100.00 | 100.00 | 100.00 |

Procedure:

Disperse hydroxyethylcellulose into 20% of the water at 80° C. Chill remaining water and add chilled water to gum dispersion, mix until homogeneous. Add remaining ingredients separately with mixing.

EXAMPLE 4—Bath Gel

This simple formulation demonstrates the utility of AMG-O in batch and shower products. AMG-O is a highly charged cationic conditioner that is completely compatible with anionic surfactants. AMG-O conditions the skin leaving it smooth, soft and satiny.

| Ingredients | % (W/W) |
|---|---|
| Sodium Lauryl Sulfate | 30.0 |
| Lauramidopropyl Betaine | 20.0 |
| Oleamidopropyl Dimethyl 2,3-Dihydroxypropyl Ammonium Chloride | 5.0 |
| Glycerine | 2.0 |
| Methyl Paraben | 0.2 |

| Ingredients | % (W/W) |
|---|---|
| Propyl Paraben | 0.1 |
| Deionized Water | 42.5 |
| Citric Acid QS to pH | 7.0 +/− 0.2 |
| Fragrance | 0.2 |
| | 100.0 |

Procedure:

Combine ingredients with mixing and adjust pH. (Gentle heat may be used to facilitate mixing).

EXAMPLE 5—Clear Dilutable Gel

One of the most unique properties of AMG-O is its ability to produce clear dilutable gels that maintain clarity on dilution.

| Ingredients | % (W/W) |
|---|---|
| Oleamidopropyl Dimethyl 2,3-Dihydroxypropyl Ammonium Chloride | 50.0 |
| Quaternium-76 Hydrolyzed Animal Protein | 25.0 |
| Stearalkonium Chloride | 25.0 |
| | 100.0 |

| Dilutions: | |
|---|---|
| Gel | Water |
| 1 | 1 |
| 1 | 2 |
| 1 | 3 |

Procedure:

Add oleamidopropyl dimethyl 2,3-dihydroxypropyl ammonium chloride and Quaternium-76 hydrolyzed animal protein together. Heat to 75° C. with mixing and add stearalkonium chloride. Mix until clear. Cool and adjust to pH 4.0-4.5. A clear gel forms on cooling.

EXAMPLE 6—Astringent Toner/After Shave Splash

| Ingredients | % (W/W) |
|---|---|
| SDA-40 B | 70.0 |
| Deionized Water | 24.0 |
| Glycerine | 1.0 |
| Oleamidopropyl Dimethyl 2,3-Dihydroxy propyl Ammonium Chloride | 3.0 |
| Fragrance | 2.0 |
| | 100.00 |

Procedure:

Combine ingredients and filter chilled.

EXAMPLE 7—Pre-Shave

| Ingredients | % (W/W) |
|---|---|
| SDA-40B (ethanol) | 87.0 |
| Propylene Glycol Dipelargonate | 10.0 |
| Oleamidopropyl Dimethyl 2,3-Dihydroxy propyl Ammonium Chloride | 3.0 |
| | 100.0 |

Procedure:

Combine ingredients with mixing

EXAMPLE 8—Clear Forming Conditioner for Moussing

| Ingredients | % (W/W) | | |
|---|---|---|---|
| | 1 | 2 | 3 |
| Deionized Water | 91.09 | 91.09 | 91.09 |
| Polyethylene Glycol/lanolin | 1.00 | 1.00 | 1.00 |
| Propylene Glycol | 2.00 | 2.00 | 2.00 |
| Methyl Paraben | 0.20 | 0.20 | 0.20 |
| Oleamidopropyl Dimethyl 2,3-Dihydroxypropyl Ammonium Chloride | 0.00 | 0.00 | 5.71 |
| Cocoamidopropyl Dimethyl 2,3-Dihydroxypropyl Ammonium Chloride | 0.00 | 5.71 | 0.00 |
| Myristylamidopropyl Dimethyl 2,3-Dihydroxypropyl Ammonium Chloride | 5.71 | 0.00 | 0.00 |
| | 100.00 | 100.00 | 100.00 |
| | 4 | 5 | 6 |
| Deionized Water | 93.09 | 93.09 | 93.09 |
| Propylene Glycol | 1.00 | 1.00 | 1.00 |
| Methyl Paraben | 0.20 | 0.20 | 0.20 |
| Oleamidopropyl Dimethyl 2,3-Dihydroxypropyl Ammonium Chloride | 5.71 | 0.00 | 0.00 |
| Cocoamidopropyl Dimethyl 2,3-Dihydroxypropyl Ammonium Chloride | 0.00 | 5.71 | 0.00 |
| Myristylamidopropyl Dimethyl 2,3-Dihydroxypropyl Ammonium Chloride | 0.00 | 0.00 | 5.71 |
| | 100.00 | 100.00 | 100.00 |

Procedure:

Combine ingredients with mild heat. Cool to room temperature, fill and charge with ingredients.

The present invention may be embodied in other specific forms without departing from the spirit or essential attributes thereof and, accordingly, reference should be made to the appended claims, rather than the specification as indicating the scope of the invention.

We claim:

1. In a clear conditioning composition for topical application to hair, the improvement comprising the presence in said composition of a quaternary ammonium salt of the formula:

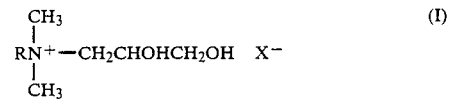

wherein R is an alkyl group of about 7 to about 24 carbon atoms or an alkylamido group of the formula:

wherein R' is an alkyl group of about 7 to about 24 carbon atoms, Y is hydrogen or an alkyl group of 1 to 6 carbon atoms, z is about 2 to about 6, and X− is a counter-ion selected from the group consisting of a carboxylate group, chloride, bromide, sulfate and phosphate.

2. A hair conditioning composition according to claim 1 wherein R is a straight chain alkyl group of 12 to 18 carbon atoms.

3. A hair conditioning composition according to claim 1, wherein R' is a straight chain alkyl group of 12 to 18 carbon atoms.

4. A hair conditioning composition according to claim 1 wherein said salt is selected from the group consisting of oleamidopropyl dimethyl 2,3-dihydroxypropyl ammonium chloride, cocoamidopropyl dimethyl 2,3-dihydroxypropyl ammonium chloride, and myristylamidopropyl dimethyl 2,3-dihydroxypropyl ammonium chloride.

5. A hair conditioning composition according to claim 1 wherein said salt is present in an amount of about 0.5 to 10 weight percent of the composition.

6. A hair conditioning composition according to claim 1 wherein said composition is in the form of a gel, mousse, lotion, spray or glaze formulation.

7. A hair conditioning composition according to claim 1 wherein said composition is in the form of a clear, aqueous dilutable gel, and said salt is oleamidopropyl dimethyl 2,3-dihydroxypropyl ammonium chloride.

8. In a conditioning composition for topical application to human skin, the improvement comprising the presence in said composition of a quaternary ammonium salt of the formula

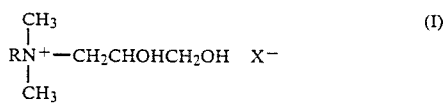

wherein R is an alkyl group of about 7 to about 24 carbon atoms or an alkylamido group of the formula:

wherein R' is an alkyl group of about 7 to 24 carbon atoms, Y is hydrogen or an alkyl group of 1 to 6 carbon atoms, z is about 2 to about 6, and X— is a counter-ion selected from the group consisting of a carboxylate group, chloride, bromide, sulfate and phosphate.

9. A skin conditioning composition according to claim 8 wherein R is a straight chain alkyl group of 12 to 18 carbon atoms.

10. A skin conditioning composition according to claim 8 wherein R' is a straight chain alkyl group of 12 to 18 carbon atoms.

11. A skin conditioning composition according to claim 8 wherein said salt is selected from the group consisting of oleamidopropyl dimethyl 2,3-dihydroxypropyl ammonium chloride, cocoamidopropyl dimethyl 2,3-dihydroxypropyl ammonium chloride, and myristylamidopropyl dimethyl 2,3-dihydroxypropyl ammonium chloride.

12. A skin conditioning composition according to claim 8 wherein said salt is present in an amount of about 0.5 to 10 weight percent of the composition.

13. A skin conditioning composition according to claim 8 wherein said composition is in the form of a cream, lotion, bath oil, liquid cleaner, body mousse, or bath gel.

14. A skin conditioning composition according to claim 8 wherein salt is dissolved in an alcoholic or hydroalcoholic vehicle.

15. A skin conditioning composition according to claim 14 wherein said composition is a clear astringent, toner, pre-electric shave conditioner, after-bath splash, cologne or perfume.

16. A method of imparting to hair properties of manageability, static control, a ease of wet and dry combing, comprising applying to the hair a clear conditioning composition containing an effective amount of a quaternary ammonium salt of the formula:

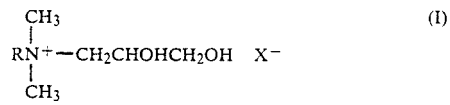

wherein R is an alkyl group of about 7 to about 24 carbon atoms or an alkylamido group of the formula:

wherein R' is an alkyl group of about 7 to 24 carbon atoms, Y is hydrogen or an alkyl group of 1 to 6 carbon atoms, z is about 2 to about 6, and X— is a counter-ion selected from the group consisting of a carboxylate group, chloride, bromide, sulfate and phosphate.

17. A method according to claim 16 wherein R is a straight chain alkyl group of 12 to 18 carbon atoms.

18. A method according to claim 16 wherein R, is a straight chain alkyl group of 12 to 18 carbon atoms.

19. A method according to claim 16 wherein said salt is selected from the group consisting of oleamidopropyl dimethyl 2,3-dihydroxypropyl ammonium chloride, cocoamidopropyl dimethyl 2,3-dihydroxypropyl ammonium chloride, and myristylamidopropyl dimethyl 2,3-dihydroxypropyl ammonium chloride.

20. A method according to claim 16 wherein said composition is applied to the hair in the form of a gel, mousse, lotion, spray, glaze or shampoo.

21. A method according to claim 16 wherein said hair is human scalp hair.

22. A method according to claim 16 wherein said salt is present in an amount of about 0.5 to 10 weight percent of the composition.

23. A method of imparting to human skin a smooth and lubricated surface with pleasant after-feel from the application of topical skin conditioners, comprising applying to the skin a conditioning composition containing an effective amount of a quaternary ammonium salt of the formula:

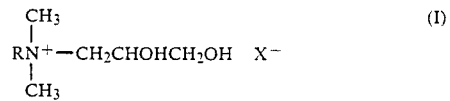

wherein R is an alkyl group of about 7 to about 24 carbon atoms or an alkylamido group of the formula:

wherein R' is an alkyl group of about 7 to 24 carbon atoms, Y is hydrogen or an alkyl group of 1 to 6 carbon atoms, z is about 2 to about 6, and X— is a counter-ion selected from the group consisting of a carboxylate group, chloride, bromide, sulfate and phosphate.

24. A method according to claim 23 wherein R is a straight chain alkyl group of 12 to 18 carbon atoms.

25. A method according to claim 23 wherein R, is a straight chain alkyl group of 12 to 18 carbon atoms.

26. A method according to claim 23 wherein said salt is selected from the group consisting of oleamidopropyl dimethyl 2,3-dihydroxypropyl ammonium chloride, cocoamidopropyl dimethyl 2,3-dihydroxypropyl ammonium chloride, and myristylamidopropyl dimethyl 2,3-dihydroxypropyl ammonium chloride.

27. A method according to claim 23 wherein said salt is present in an amount of about 0.5 to 10 weight percent of the composition.

28. A method according to claim 23 wherein the composition is applied to the skin in the form of a cream, lotion, bath oil, liquid cleaner, body mousse, or bath gel.

* * * * *